United States Patent [19]

Hasegawa et al.

[11] Patent Number: 4,918,208

[45] Date of Patent: Apr. 17, 1990

[54] PROCESS FOR PRODUCING 7-DIMETHYLAMINO-6-DEMETHYL-6-DEOXYTETRACYCLINE

[75] Inventors: Ryoichi Hasegawa, Yono; Hiroaki Ohno, Tokyo; Kazuaki Sano, Hoya; Yoshinori Saito, Yono, all of Japan

[73] Assignee: Nippon Kayaku Kabushiki Kaisha, Tokyo, Japan

[21] Appl. No.: 222,886

[22] Filed: Jul. 22, 1988

[30] Foreign Application Priority Data

Jul. 28, 1987 [JP] Japan ................................ 62-186563
Aug. 18, 1987 [JP] Japan ................................ 62-203540

[51] Int. Cl.⁴ ............................................. C01D 99/29
[52] U.S. Cl. ..................................... 552/205; 552/206
[58] Field of Search ............... 260/351.6, 351.2, 351.5, 260/351.3; 552/206

[56] References Cited

U.S. PATENT DOCUMENTS

| | | | |
|---|---|---|---|
| 3,226,436 | 12/1965 | Petisi et al. ........................ | 260/351.3 |
| 3,403,179 | 9/1968 | Zambrano ......................... | 260/351.3 |
| 3,515,717 | 6/1970 | Cha et al. ......................... | 260/351.6 |
| 3,725,400 | 4/1973 | Voser ................................. | 260/351.3 |

FOREIGN PATENT DOCUMENTS

| | | | |
|---|---|---|---|
| 428380 | 9/1968 | France .............................. | 260/351.3 |
| 50-37666 | 12/1975 | Japan ................................ | 260/351.3 |

OTHER PUBLICATIONS

J. Med. Chem., vol. 10, pp. 44, (1967), Fr. Add. No. 92,088.
I & EC Product Research & Development, 7, 107, (1968), "Amberlite XAD".

*Primary Examiner*—Richard L. Raymond
*Assistant Examiner*—Raymond Covington
*Attorney, Agent, or Firm*—Henry C. Nields

[57] ABSTRACT

A process for producing 7-dimethylamino-6-demethyl-6-deoxytetracycline (minocycline) which comprises treating the reaction liquid containing minocycline and formaldehyde with hydroxylamine or urea, the reaction liquid being obtained after reductive methylation of 7-amino-6-demethyl-6-deoxytetracycline by using aldehyde, then subjecting the reaction liquid to an adsorption treatment with a nonionic adsorption resin (adsorbent), and subsequently eluting the intended product adsorbed to the adsorbent.

4 Claims, No Drawings

PROCESS FOR PRODUCING 7-DIMETHYLAMINO-6-DEMETHYL-6-DEOXYTETRACYCLINE

FIELD OF THE INVENTION AND RELATED ART STATEMENT

This invention relates to a process for producing a medicament. More particularly, it relates to a process for producing 7-dimethylamino-6-demethyl-6-deoxytetracycline (hereinafter referred to as "minocycline"), an antibiotic substance of the tetracycline family.

DESCRIPTION OF THE RELATED ART

Minocycline is an antibiotic substance useful as a medicament. Typical known methods for synthesizing minocycline include (1) reductive dimethylamination of 7-nitro-6-demethyl-6-deoxytetracycline with formaldehyde (U.S. Pat. No. 3,226,436; J. Med. Chem., 10, 44 (1967); JP-B-42-8380, (2) reductive dimethylamination of 7-[1,2-bis(carbobenzyloxy)hydrazino]-6-demethyl-6-deoxytetracycline with formaldehyde (U.S. Pat. No. 3,403,179; JP-B-50-37666), and (3) reductive dimethylamination of 7-(4-sulfophenylazo)-6-demethyl-6-deoxytetracycline with formaldehyde (Fr. Add. No. 92,088). Minocycline obtained by any of the aforementioned methods is isolated by pouring the reaction liquid after the reductive dimethylamination (wherein usually alcohols such as methyl cellosolve, methanol and ethanol are used as a solvent) into a large amount of a solvent which does not dissolve minocycline, such as ether or acetone, to precipitate crystals of minocycline (namely a dilution method) or by extracting it with a water-immiscible organic solvent such as chloroform or ethyl acetate from the reaction liquid which has been made neutral to prevent salt formation between minocycline and acids (namely an extraction method). With regard to removal of formaldehyde remaining in the reaction liquid, no description is given in the prior reference. Since residual formaldehyde exerts an adverse effect of forming by-products, particularly in aqueous medium, by reacting with minocycline, it is preferably removed as completely as possible.

Accordingly, development of an effective process for producing minocycline of low impurity content is eagerly awaited which can replace the above-mentioned dilution or extraction method, both of which requires the use of a large amount of organic solvent.

SUMMARY OF THE INVENTION

The present inventors has made extensive studies to establish a process for obtaining minocycline of a high purity in a high yield which is free from the adverse effect of residual formaldehyde mentioned above, and resultantly attained the present invention.

Thus, according to the present invention, there is provided a process for producing 7-dimethylamino-6-demethyl-6-deoxytetracycline (minocycline) which comprises treating the reaction liquid containing minocycline and formaldehyde with hydroxyamine or urea, the reaction liquid being obtained after reductive methylation of 7-amino-6-demethyl-6-deoxytetracycline by using aldehyde, then subjecting the reaction liquid to an adsorption treatment with a nonionic adsorption resin (adsorbent), and subsequently eluting the intended product adsorbed to the adsorbent.

DESCRIPTION OF PREFERRED EMBODIMENTS

The process of the present invention will now be described in detail below.

As described above, the processes for producing minocycline generally include reductive dimethylation of 7-amino-6-demethyl-6-deoxytetracycline, which, for example, is obtained by hydrogenation of 7-nitro-6-demethyl-6-deoxytetracycline, 7-[1,2-bis(carbobenzyloxy)-hydrazino]-6-demethyl-6-deoxytetracycline or 11a-chloro-6-demethyl-6-deoxy-7-(p-sulfophenylazo)-tetracycline with hydrogen, using excess of formaldehyde but, after completion of the reaction, it is preferable to remove residual formaldehyde effectively from the reaction liquid to suppress the formation of by-products.

Although several methods are already known for removing formaldehyde from a solution containing it and other compounds, it has been found by the present inventors that treatment with hydroxylamine or urea gives a particularly good result. Since it is already known that hydroxylamine reacts with carbonyl compounds, it was expected that it would react also with minocycline which has carbonyl groups. Contrary to the expectation, however, no indication of a reaction between hydroxylamine and minocycline was observed.

The amount of hydroxylamine or urea to be used is usually 0.5 to 10 moles, preferably 0.8 to 2 moles, per mole of formaldehyde used in excess. Hydroxylamine may be used in any of the forms including hydrochloride, sulfate, organic acid salts and free amine.

For treating the reaction liquid containing minocycline, formaldehyde and other impurities (wherein alcoholic solvents such as methyl cellosolve, methanol and ethanol are usually employed), with hydroxylamine or urea, there may be mentioned a method comprising adding hydroxylamine or urea directly to the reaction liquid, and one comprising dissolving hydroxylamine or urea in water or other solvents beforehand and then pouring to the solution, under stirring, the solution of minocycline containing formaldehyde.

The treatment of the reaction liquid with hydroxylamine or urea may be usually carried out at 0° to 50° C. for 5 minutes to 10 hours.

There is no particular limitation as to the solvent used for dissolving hydroxylamine or urea. Preferred examples of the solvent include water; alcohols such as methanol, butanol, methyl cellosolve and the like; aprotic polar solvents such as dimethylformamide, dimethyl sulfoxide and the like; esters such as ethyl acetate, butyl acetate and the like; ketones such as acetone, methyl ethyl ketone and the like; halogenated hydrocarbons such as methylene chloride, chloroform and the like; and ethers such as tetrahydrofuran, dioxane and the like.

The reaction liquid at the time of being treated with hydroxylamine or urea may be either acidic, neutral or basic. However, treatment under acidic to neutral conditions gives better results. If insoluble matter separates out after the treatment, it may be removed by filtration. Particularly, when urea is used as a treating agent an insoluble polymer tends to be formed, which is preferably filtered off.

The reaction liquid treated as described above is then subjected to an adsorption treatment with an adsorbent.

In the present invention, a nonionic adsorption resin (high porous polymer) is used as the adsorbent. Typical examples thereof include styrene-divinylbenzene type copolymers, substituted styrene-divinylbenzene type copolymers; methacrylic acid type polymers, styrene-allylacrylate type copolymers, other vinyl polymers or copolymers, and the like polymers which have been formed into granules. As an index to the porosity of a nonionic adsorption resin, there is used the specific surface area. A nonionic adsorption resin having a specific surface area of 30–2,000 $m^2/g$ are suitably used and those having the area of 100–1,000 $m^2/g$ are particularly preferable. The adsorption of minocycline to a nonionic adsorption resin is estimated to be caused mainly by van der Waals force. As specific examples of such adsorbents, there may be mentioned Diaion ® HP-10, HP-20, HP-21, HP-30, HP-40, HP-50, SP-206, SP-207, SP-800, SP-900, HP-MG1MG and HP-MG2MG (all mfd. by Mitsubishi Chemical Industries Ltd.) and Amberlite ® XAD-1, XAD-2, XAD-4, XAD-5 and XAD-7 (all mfd. by Rohm and Haas Co.), but they are not limited thereto. With regard to a nonionic adsorption resin used suitably in the process of the present invention, detail descriptions are given, for example, in the following references:

I & EC Product Research and Development, 7, 107 (1968);

"Amberlite XAD", published by Japan Organo Co., Ltd.);

U.S. Pat. No. 3,725,400.

The suitable amount of adsorbent to be used is 10–100 volumes relative to unit weight of minocycline present in the solution to be treated (namely, 10–100 ml/1 g minocycline).

Before being subjected to such an adsorption treatment, the reaction liquid treated with hydroxylamine or urea is preferably diluted with water to form an aqueous solution. If insoluble matter is formed by dilution with water it is removed by filtration. The solution is then adjusted to a pH of 3–9, preferably 5–8, and subjected to adsorption with the aforesaid adsorbent. When the pH of the solution is not higher than 3, adsorption of minocycline to the adsorbent is poor, whereas when it is higher than 9 minocycline is liable to decompose, when the solution to be treated has a pH of 5–8, 98% of more of minocycline present in the solution are adsorbed suitably to the adsorbent. The minocycline-containing aqueous solution to be subjected to the adsorption may contain water-soluble organic solvents such as methanol, ethanol, methyl cellosolve, DMF and the like and it is preferably prepared such that water amounts to at least one third, more preferably one half, of the total solution. The adsorption to the adsorbent can be accomplished either by a column method or by a batch method, the former method is preferable. The adsorption may usually be carried out at room temperature (about 10°–50° C.). After minocycline has been adsorbed to the adsorbent, it is first developed with a large amount of water to elute contaminants other than substances of the tetracycline family. At this time, by-products formed during the reductive dimethylation, for example, amines formed by the decomposition of azo groups, reaction products between formaldehyde and hydroxylamine, reaction products between formaldehyde and urea, and the like substances, are eluted. Of course, the contaminants may also be removed batchwise by washing with water. Thereafter, the purity of minocycline can be enhanced by washing with a dilute aqueous solution of an organic solvent.

The eluent used for eluting minocycline adsorbed to the adsorbent is a polar organic solvent miscible with water. Particularly preferred is an organic solvent to which an acid has been added in an equivalent moles or more to one mole of minocycline estimated to have been adsorbed. The amount of eluent to be used is 1–10 times by volume, preferably 1.5–3 times by volume, that of the adsorbent.

As examples of the polar organic solvent, there may be mentioned alkanols such as methanol, ethanol, isopropanol and the like; alkoxyalkanols such as 2-methoxyethanol, 2-ethoxyethanol, 1-ethoxypropanol and the like; glycols such as ethylene glycol, propylene glycol and the like; and aprotic polar solvents such as dimethylformamide, dimethylacetamide, dimethylimidazolidinone, dimethyl sulfoxide and the like. Particularly preferred are lower alkanols. The acids added to the organic solvent are mineral acids such as hydrochloric acid, hydrobromic acid or sulfuric acid or organic acids such as oxalic acid, and are preferably hydrochloric acid or sulfuric acid. The amount of the acid is preferably about 1.5 to 3 moles per mole of minocycline estimated to have been adsorbed. The polar organic solvent may contain water.

The eluate containing minocycline thus obtained is concentrated and adjusted to a pH of 4–8 to obtain crystals of minocycline (hydrate). Minocycline (hydrate) thus obtained has a sufficient purity to be used as a medicament. If necessary, minocycline having more enhanced purity can be obtained by repeating the adsorption treatment alone according to the above-mentioned process. Moreover, a purified product can be obtained by converting minocycline into its hydrochloride, which is then dissolved in a mixture of an alcohol such as methanol, ethanol etc with water to obtain a solution containing minocycline at a pH of 0.1–2.5 and the solution is then adjusted to a pH of 3.5–4.5 to recrystallize its hydrochloride.

After elution of minocycline, the adsorbent can be regenerated to the initial state merely by washing it with a large amount of neutral water. In the process of the present invention, the adsorbing capacity of the adsorbent was maintained even after an endurance test of repeated 50 times.

The present invention will further be described in detail below with reference to Examples.

EXAMPLE 1

According to the method described in Fr. Add. No. 92,088, 30 g of 11a-chloro-6-demethyl-6-deoxy-7-(4-sulfophenylazo)tetracycline and 30.8 g of aqueous 37% formaldehyde aqueous solution were subjected to hydrogenation to obtain 7-amino-6-demethyl-6-deoxytetracycline and reductive methylation thereof in 600 ml of methyl cellosolve and in the presence of a palladium-on-carbon catalyst. After the catalyst had been filtered off, 640 g of a yellowish orange methyl cellosolve solution containing 16.3 g of minocycline (free form) was obtained. The solution contained minocycline (the intended product) and also 4-dimethylaminobenzenesulfonic acid, formaldehyde and other impurities.

The solution was dissolved in 2000 ml of water containing 15.7 g of hydroxylamine sulfate, then stirred at room temperature (20° C.) for about 20 minutes, and adjusted to pH 7.4 with 20% sodium hydroxide aqueous solution. The solution was then passed through a column containing 400 ml of Diaion ® HP-20 resin (a high porous polymer, styrene-divinylbenzene copolymer, specific surface area: 720 m$^2$/g) to effect adsorption (20° C.). Thereafter, development and elution were carried out by using 10 l of deionized water to elute and remove by-products and impurities other than tetracyclines. Scarcely any effluence of minocycline was observed during the operation.

Minocycline adsorbed to the adsorbent was developed and eluted with 1500 ml of a methanol solution containing 7.5 g of concentrated hydrochloric acid to give 1300 ml of an eluate containing 16.0 g (98% recovery) of minocycline. Liquid chromatographic analysis showed a purity of 95% or more (areal percentage). The eluate was concentrated and adjusted to pH 4.0 with 10% aqueous sodium hydroxide solution, whereby a pale yellow precipitate separated out. It was then separated by filtration and dried under vacuum at room temperature (20° C.) to give 15.3 g of minocycline monohydrochloride dihydrate as pale yellow powder. Analysis of the product by liquid chromatography showed a purity of 99.2% (potency according to U.S. Pharmacopoeia: 910 μg/mg in terms of anhydride). The recovery yield of minocycline after reductive dimethylation was 80.9%. The by-product formed in the aqueous solution by the action of residual formaldehyde amounted to 0.04%.

The mother liquor obtained after filtration of the precipitate formed by concentration the solution eluted from the adsorbent column followed by pH adjustment as described above contains a considerable amount of minocycline. The mother liquor (containing 2.79 g of minocycline) was adjusted to pH 7.4 with 20% sodium hydroxide aqueous solution and subjected again to adsorption with Diaion ® HP-20. Elution with methanol-hydrochloric acid conducted in the same manner as described above gave minocycline in a recovery of 90%.

EXAMPLE 2

In the same manner as in Example 1 except that the adsorbent used was altered from Diaion ® HP-20 to Diaion ® SP-900, 15.5 g of minocycline monohydrochloride dihydrate was obtained. Analysis of the product by liquid chromatography showed a purity of 95.1% (potency: 876 μg/mg in terms of anhydride).

EXAMPLE 3

According to the method described in JP-B-42-8380, 10 g of 7-nitro-6-demethyl-6-deoxytetracycline sulfate was subjected to hydrogenation to obtain 7-amino-6-demethyl-6-deoxytetracycline and reductive dimethylation thereof, with 37% formaldehyde aqueous solution added thereto, in 200 ml of methyl cellosolve and in the presence of a palladium-on-carbon catalyst. After completion of the reaction, the catalyst was filtered off. Resultantly, 280 g of a yellow solution containing 7.0 g of minocycline (as the free form) was obtained.

The solution was then dissolved in 2000 ml of water containing 11.9 g of hydroxylamine sulfate. The resulting solution was kept at room temperature (20° C.) for 30 minutes, then adjusted to pH 6.8 with 20% sodium hydroxide aqueous solution and subjected to adsorption wit Diaion ® HP-20 followed by elution in the same manner as in Example 1. The eluate thus obtained was concentrated and then adjusted to pH 4.0 to give 5.3 g of minocycline monohydrochloride dihydrate.

Analysis of the product by liquid chromatography showed a purity of 99.1% (potency: 909 μg/mg in terms of anhydride).

EXAMPLE 4

A reaction was carried out in the same manner as in Example 1 to give a reaction liquid containing minocycline (18.73 g as the free form), formaldehyde, and other substances. In a 3-liter beaker were placed 2 l of water and 10.7 g of urea and, under stirring, the above reaction liquid was gradually added thereto at room temperature (20° C.). After 6 hours treatment under the condition, light brown insoluble matter separated out. The insoluble matter was filtered off and the filtrate was gradually adjusted to neutral with 20% sodium hydroxide aqueous solution. The resulting treated reaction liquid was subjected to an adsorption treatment using Diaion ® HP-20 as an adsorbent to make minocycline adsorbed thereto. After water washing and nextly eluting with 1500 ml of methanol containing 7.5 g of concentrated hydrochloric acid, methanol was distilled off from the eluate thus obtained. The eluate was then adjusted to pH 4 to give white crystals. The crystal was dried at room temperature (20° C.) under reduced pressure to give 17.2 g of minocycline monohydrochloride dihydrate. (The recovery yield was 79.3%). Analysis of the product by liquid chromatography showed a purity of 99.0%. The content of the by-product formed in aqueous medium by the action of residual formaldehyde was 0.06%.

EXAMPLE 5

The procedure in Example 1 were repeated except that 1 l of Amberlite ® XAD-7 (high porous polymer, methacrylic acid type polymer, specific surface area: 450 m$^2$/g, average pore diameter: 90 Å) was used as the adsorbent in place of Diaion ® HP-20, to obtain 16.3 g of minocycline monohydrochloride dihydrate.

Analysis of the product by liquid chromatography showed a purity of 98.1% (potency: 880 μg/mg in terms of anhydride).

EXAMPLE 6

According to the method described in Fr. Add. No. 92,088, 30 g of 11a-chloro-6-demethyl-6-deoxy-7-(p-sulfophenylazo)tetracycline was hydrogenated to obtain 7-amino-6-demethyl-6-deoxytetracycline by using a palladium-on-carbon catalyst in 600 ml of methyl cellosolve, then 30.8 g of 37% formaldehyde aqueous solution was added to the reaction liquid and the mixture was subjected to reductive methylation in a hydrogen atmosphere.

After completion of the reaction, the insoluble catalyst was filtered off to obtain a reaction liquid containing minocycline and formaldehyde. In a 3-liter beaker were placed 15.7 g of hydroxylamine semisulfate and 2 l of water and then, under stirring, the above reaction liquid was gradually added thereto at room temperature (20° C.). The final mixture had a pH of 1.5. After 15 minutes of treatment under the conditions (under stirring), the mixture was gradually adjusted to neutral (pH: 7.05) by the use of 20% sodium hydroxide aqueous solution.

The resulting reaction liquid thus treated was then treated with an adsorbent (Diaion ® HP-20) to make minocycline adsorbed thereto. After washing with water and nextly eluting with methanol containing hydrochloric acid, methanol was distilled off from the eluate obtained. The eluate was then adjusted to pH 4 to obtain minocycline as white crystal. The crystal was filtered off, and the product issued into the filtrate was recovered from the filtrate by column adsorption. The product was collected and dried under reduced pressure at room temperature (20° C.) to give 17.8 g of minocycline monohydrochloride dihydrate.

Analysis of the product by liquid chromatography revealed a purity of 99.1%. The content of the by-product formed by the action of residual formaldehyde on minocycline was 0.04%.

What is claimed is:

1. A process for producing 7-dimethylamino-6-demethyl-6-deoxytetracycline (minocycline) which comprises treating the reaction liquid containing minocycline and formaldehyde with hydroxylamine or urea, the reaction liquid being obtained after reductive methylation of 7-amino-6-demethyl-6-deoxytetracycline by using aldehyde, then subjecting the reaction liquid to an adsorption treatment with a nonionic adsorption resin (adsorbent), and subsequently eluting the intended product adsorbed to the adsorbent.

2. A process according to claim 1 wherein a nonionic adsorption resin has a specific surface area of 30–2,000 $m^2/g$.

3. A process according to claim 1 wherein the intended product adsorbed to the adsorbent is eluted with an organic solvent containing hydrochloric acid or sulfuric acid.

4. A process according to claim 1 wherein impurities and by-products other than the intended product are removed by elution with water prior to said elution of the intended product adsorbed to the adsorbent.

* * * * *